United States Patent
Kobayashi

(10) Patent No.: US 10,702,145 B2
(45) Date of Patent: Jul. 7, 2020

(54) OPHTHALMOLOGIC APPARATUS

(71) Applicant: TOPCON CORPORATION, Tokyo (JP)

(72) Inventor: Mariko Kobayashi, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 179 days.

(21) Appl. No.: 16/083,782

(22) PCT Filed: Jan. 13, 2017

(86) PCT No.: PCT/JP2017/001101
§ 371 (c)(1),
(2) Date: Sep. 10, 2018

(87) PCT Pub. No.: WO2017/154348
PCT Pub. Date: Sep. 14, 2017

(65) Prior Publication Data
US 2019/0076012 A1    Mar. 14, 2019

(30) Foreign Application Priority Data
Mar. 8, 2016  (JP) .................... 2016-044972

(51) Int. Cl.
*A61B 3/10* (2006.01)
*A61B 3/107* (2006.01)
(Continued)

(52) U.S. Cl.
CPC ............... *A61B 3/102* (2013.01); *A61B 3/10* (2013.01); *A61B 3/107* (2013.01); *A61B 3/135* (2013.01);
(Continued)

(58) Field of Classification Search
CPC .. A61B 3/102; A61B 3/14; A61B 3/12; A61B 5/0066; A61B 3/10; A61B 3/0008; A61B 3/13; A61B 3/0058
(Continued)

(56) References Cited

U.S. PATENT DOCUMENTS

2012/0281184 A1* 11/2012 Torii .................... A61B 3/0025
                                                                351/206
2013/0188140 A1    7/2013  Bagherinia et al.
2016/0038021 A1    2/2016  Bagherinia et al.

FOREIGN PATENT DOCUMENTS

JP    2012232034    11/2012
JP    2015504740     2/2015

OTHER PUBLICATIONS

English translation of International Search Report dated Apr. 11, 2017 in PCT/JP2017/001101.

* cited by examiner

*Primary Examiner* — Hung X Dang
(74) *Attorney, Agent, or Firm* — Xsensus LLP

(57) ABSTRACT

An ophthalmologic apparatus according to an exemplary embodiment acquires data by OCT scanning of the anterior eye segment. The apparatus generates distribution information of a predetermined parameter in the anterior eye segment by analyzing the data. The apparatus acquires a front image of the anterior eye segment at the time of the data being acquired. The apparatus stores the first distribution information and the first front image both corresponding to the first time, and the second distribution information and the second front image both corresponding to the second time. The apparatus calculates the positional difference between the first front image and the second front image.

(Continued)

The apparatus applies registration to the first distribution information and the second distribution information based on the positional difference.

13 Claims, 7 Drawing Sheets

(51) Int. Cl.
    *A61B 3/135*     (2006.01)
    *G01B 9/02*     (2006.01)
    *A61B 3/15*     (2006.01)
    *A61B 3/00*     (2006.01)
    *G01N 21/47*     (2006.01)

(52) U.S. Cl.
    CPC ............ *A61B 3/152* (2013.01); *G01B 9/0203* (2013.01); *G01B 9/02004* (2013.01); *G01B 9/02091* (2013.01); *A61B 3/0025* (2013.01); *G01B 2290/35* (2013.01); *G01N 21/4795* (2013.01)

(58) Field of Classification Search
    USPC .................................. 351/246, 206, 221, 205
    See application file for complete search history.

OPHTHALMOLOGIC APPARATUS

CROSS-REFERENCE TO RELATED APPLICATIONS

This application is a national stage (under 35 U.S.C. 371) of International Patent Application No. PCT/JP2017/001101, filed Jan. 13, 2017, claiming priority to Japanese Patent Application No. 2016-044972, filed Mar. 8, 2016, both of which are herein incorporated by reference in their entirety.

FIELD

Embodiments described herein relate to an ophthalmologic apparatus.

BACKGROUND

Diagnostic imaging serves an important role in the field of ophthalmology and the utilization of optical coherence tomography (OCT) has advanced in recent years. OCT is used not only for acquisition of B-mode images and three dimensional images of a subject's eye but also for construction of front images (also referred to as en-face images) such as C-mode images and shadowgrams, for construction of blood vessel emphasized images (also referred to as angiograms), for blood flow measurement, for evaluation of the size and/or morphology of an ocular tissue, and the like.

A cornea is a typical ocular tissue that can be evaluated using OCT. For example, Japanese Unexamined Patent Application Publication (Translation of PCT Application) No. 2015-504740 discloses a technique for evaluating an anterior eye segment parameter such as corneal thickness and curvature. The technique can be used for checking time-dependent change of the cornea in evaluation of surgery, evaluation of treatment, prognosis management, and the like. Checking the time-dependent change is performed, for example, by comparing measurement results (e.g., corneal thickness map) obtained at mutually different times. An example of the mutually different times includes a time before surgery and a time after the surgery.

In such comparative evaluation, the accuracy of registration of maps is important. In order to satisfy this requirement, it is conceivable to increase the precision of alignment at the time of measurement to ensure the reproducibility of the measurement position. However, there are problems in this method such as the followings: the alignment may take a long time; the alignment may be affected by involuntary eye movements etc.; the reference of alignment (e.g., corneal apex) may deviate due to deformation of ocular tissues by having undergone surgery.

In this regard, the technique described in Japanese Unexamined Patent Application Publication (Translation of PCT Application) No. 2015-504740 makes it possible to perform inter-map registration by specifying the corneal apex position from an approximate curved surface of the corneal shape obtained using OCT even if alignment at the time of measurement is deviated to a certain degree. However, the conventional technique cannot be employed in an appropriate manner for comparative observation before and after surgery that may bring about cornea deformation.

SUMMARY

An object of the ophthalmologic apparatus according to the present invention is to accurately grasp the time-dependent change of anterior eye segment parameters irrespective of the presence or absence of the shape change of cornea, or the degree of the shape change of cornea.

An ophthalmologic apparatus of an exemplary embodiment includes a data acquisition device, a distribution information generator, a front image acquisition device, a storage, a positional difference calculator, and a registration processor. The data acquisition device acquires data by scanning an anterior eye segment of a subject's eye using optical coherence tomography. The distribution information generator generates distribution information representing a distribution of a predetermined parameter in the anterior eye segment by analyzing the data. The front image acquisition device acquires a front image of the anterior eye segment at a time of the data being acquired. The storage stores first distribution information generated from first data acquired at a first time, a first front image at a time of the first data is being acquired, second distribution information generated from second data acquired at a second time, and a second front image at a time of the second data is being acquired. The positional difference calculator calculates a positional difference between the first front image and the second front image. The registration processor applies registration to the first distribution information and the second distribution information based on the positional difference.

DETAILED DESCRIPTION

Figure 1:
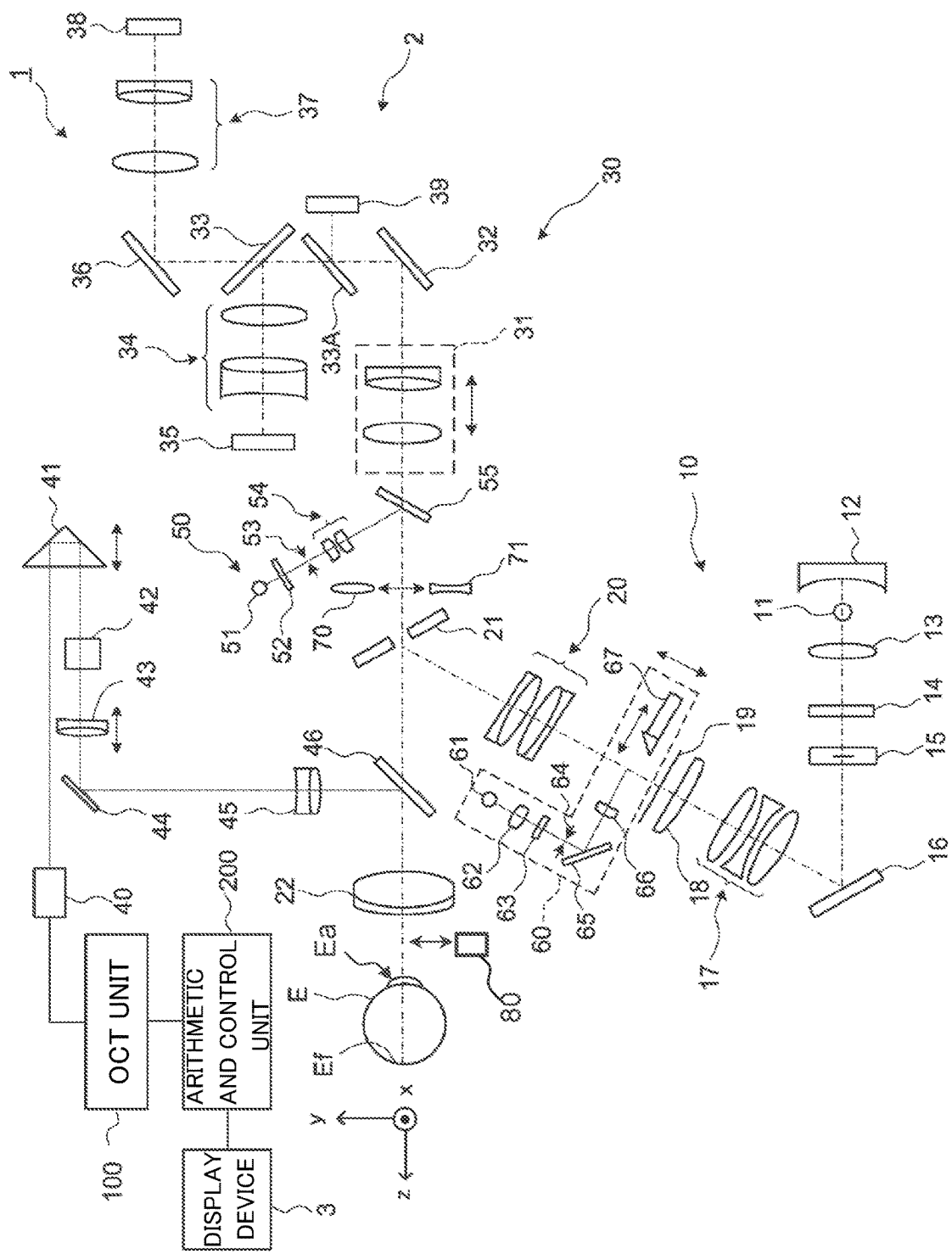
FIG. 1 is a schematic diagram illustrating an example of the configuration of the ophthalmologic apparatus according to the embodiment.

Some embodiments of the present invention will be described in detail with referring to the drawings. The ophthalmologic apparatus according to any one of the embodiments has a function of performing anterior eye segment OCT and a function of acquiring front images of anterior eye segments. The latter function can be realized, for example, by a fundus camera (also referred to as a retinal camera), a slit lamp microscope, an ophthalmologic surgical microscope, an anterior eye segment photographing camera, or the like. Further, a front image can be constructed from data acquired by the anterior eye segment OCT.

Hereinafter, an example of a multi-modality apparatus in which swept source OCT and a fundus camera are combined will be described; however embodiments are not limited to such a multi-modality apparatus.

<Configuration>

As shown in FIG. 1, the ophthalmologic apparatus 1 includes the fundus camera unit 2, the OCT unit 100 and the arithmetic and control unit 200. The fundus camera unit 2 is provided with an optical system and mechanism for acquiring front images of the subject's eye E (the anterior eye segment Ea, the fundus Ef). The OCT unit 100 includes an optical system and a mechanism for performing OCT. The arithmetic and control unit 200 includes one or more processors that perform various calculations and controls. In addition to these, ophthalmologic apparatus 1 also includes a member for supporting the face of the subject (e.g., a chin rest, a forehead rest) and a lens unit for switching the sites to be imaged by OCT (e.g., an attachment for an anterior eye segment OCT).

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the anterior eye segment Ea and the fundus Ef. Images acquired by the fundus camera unit 2 include front images such as observation images and photographed images. An observation image is obtained by capturing a moving image using near-infrared light. A photographed image is a still image obtained by using flash light.

The fundus camera unit 2 includes the illumination optical system 10 and the photographing optical system 30. The illumination optical system 10 projects illumination light onto the subject's eye E. The photographing optical system 30 detects the returning light of the illumination light from the subject's eye E. The measurement light incident from the OCT unit 100 is directed to the subject's eye E through the optical path in the fundus camera unit 2, and the returning light thereof is directed to the OCT unit 100 through the same optical path.

The observation light source 11 of the illumination optical system 10 outputs continuous light that contains a near-infrared component. The continuous light is referred to as observation illumination light. The observation illumination light is reflected by the reflection mirror 12 having a concave reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the anterior eye segment Ea or the fundus Ef). The returning light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the returning light passes through the half mirror 33A, is reflected by the dichroic mirror 33, and forms an image on the light receiving surface of the image sensor 35 by the condenser lens 34. The image sensor 35 detects the returning light at a predetermined frame rate. Note that the focus of the photographing optical system 30 is adjusted with respect to the anterior eye segment Ea or the fundus Ef.

The photographing light source 15 outputs flash light that contains a visible component (and a near-infrared component). The flash light is called photographing illumination light. The photographing illumination light passes through the same route as that of the observation illumination light and is projected onto the fundus Ef. The returning light of the photographing illumination light from the subject's eye E passes through the same route as that of the returning light of the observation illumination light, is guided to the dichroic mirror 33, passes through the dichroic mirror 33, is reflected by the mirror 36, and forms an image on the light receiving surface of the image sensor 38 by the condenser lens 37.

The LCD 39 displays a fixation target and a visual target used for visual acuity measurement. Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

The alignment optical system 50 generates an alignment indicator used for the alignment of the optical system with respect to the subject's eye E. The alignment light output from the LED 51 travels through the diaphragms 52 and 53 and the relay lens 54, is reflected by the dichroic mirror 55, and passes through the aperture part of the aperture mirror 21. The light having passed through the aperture part of the aperture mirror 21 penetrates the dichroic mirror 46 and is projected onto the subject's eye E by the objective lens 22. The cornea reflection light of the alignment light passes through the same route as that of the returning light of the observation illumination light and is guided to the image sensor 35. Based on the received image (called the alignment indicator image), manual alignment and/or automatic alignment can be performed.

The focus optical system 60 generates a split indicator used for the focus adjustment with respect to subject's eye E. The focus optical system 60 is moved along the optical path of the illumination optical system 10 (called the illumination optical path) in conjunction with the movement of the photography focusing lens 31 along the optical path of the photographing optical system 30 (called the photographing optical path). The reflection rod 67 can be inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, penetrates the dichroic mirror 46, and is refracted by the objective lens 22, thereby being projected onto the fundus Ef. The fundus reflection light of the focus light passes through the same route as that of the cornea reflection light of the alignment light and is guided to the image sensor 35. Based on the image (called the split indicator image), manual alignment and/or automatic alignment can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT. The dichroic mirror 46 reflects the light of wavelength bands used for OCT and transmits the light for fundus photography. Listed from the OCT unit 100 side, the collimator lens unit 40, the optical path length (OPL) changing device 41, the optical scanner 42, the OCT focusing lens 43, the mirror 44, and the relay lens 45 are placed in the optical path for OCT.

The optical path length changing device 41 is movable in the directions indicated by the arrow in FIG. 1 to change the optical path length for OCT. The change in the OCT optical path length can be utilized for correcting the optical path length according to the axial length, for adjusting the interference condition, and the like. The optical path length changing device 41 includes a corner cube and a mechanism for moving the corner cube.

The optical scanner 42 is placed at a position optically conjugate with the pupil of the subject's eye E. The optical scanner 42 deflects the measurement light LS that travels along the OCT optical path. The optical scanner 42 is, for example, a galvano scanner capable of two dimensional scanning.

The OCT focusing lens 43 is moved along the optical path of the measurement light LS in order to adjust the focus of the OCT optical system. The movement of the photography focusing lens 31, the movement of the focus optical system 60, and the movement of the OCT focusing lens 43 can be controlled in an interlocking manner.

The ophthalmologic apparatus 1 includes the auxiliary lens unit 80. The auxiliary lens unit 80 can be placed on the front side of the objective lens 22 (i.e., the subject's eye E side). The auxiliary lens unit 80 includes, for example, a lens group that has a positive refractive power. The auxiliary lens unit 80 is removed from the optical path when applying OCT to the fundus Ef and is inserted into the optical path when applying OCT to the anterior eye segment Ea. The movement (that is, insertion into and removal from the optical path) of the auxiliary lens unit 80 is performed electrically or manually.

<OCT Unit 100>

Figure 2:
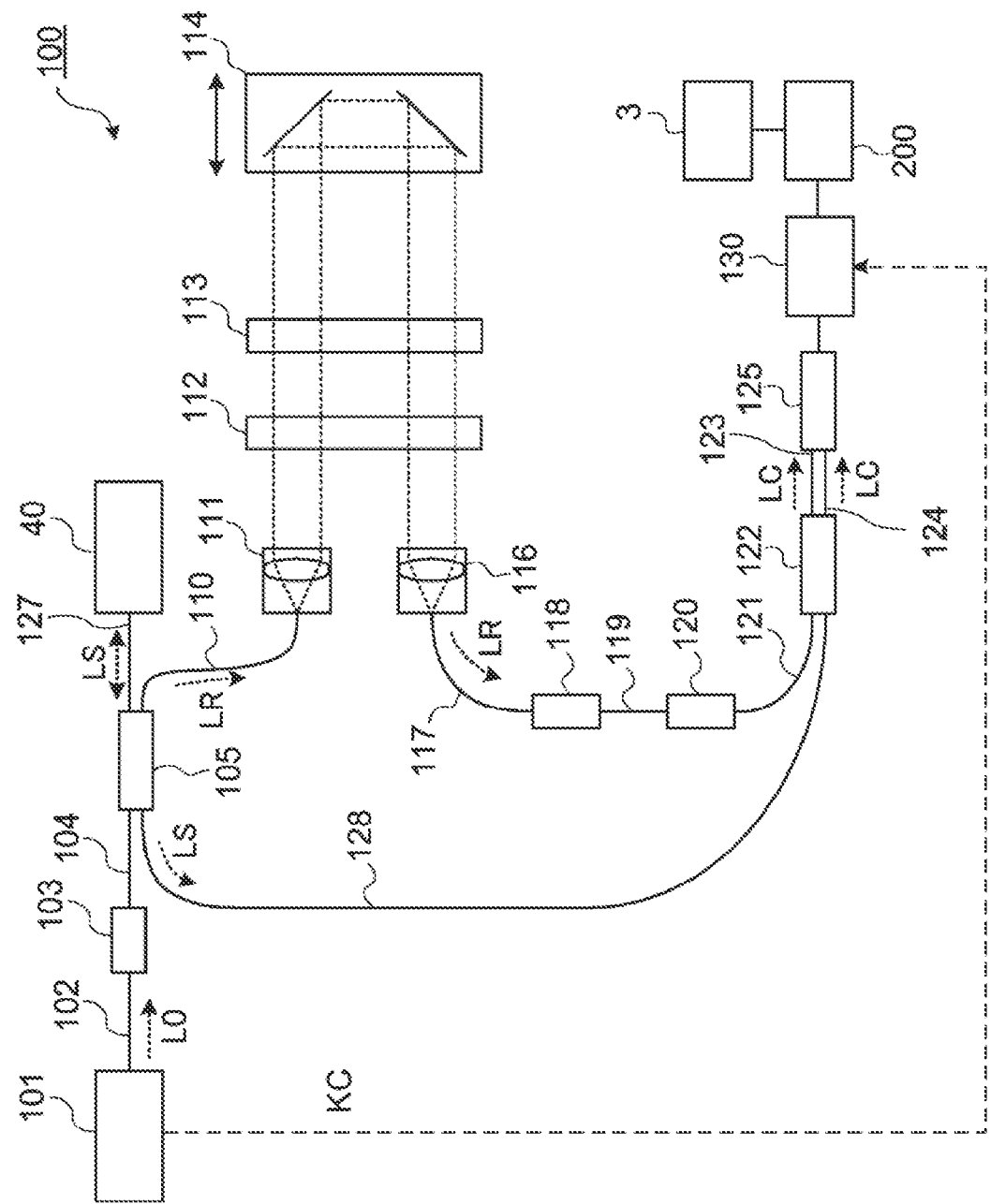
FIG. 2 is a schematic diagram illustrating an example of the configuration of the ophthalmologic apparatus according to the embodiment.

As illustrated in FIG. 2, the OCT unit 100 is provided with the optical system for performing swept source OCT. The optical system includes an interference optical system. The interference optical system is configured to split the light emitted from the light source of wavelength tunable type (also called wavelength swept type) into measurement light and reference light, superpose the returning light of the measurement light from the subject's eye E and the reference light having traveled through the reference optical path to generate interference light, and detect the interference light. The detection result (i.e., detection signal) obtained by the interference optical system is sent to the arithmetic and control unit 200.

The light source unit 101 includes, for example, a near-infrared tunable laser configured to change the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR.

The reference light LR is guided through the optical fiber 110 to the collimator 111, is converted into a parallel light beam, travels through the optical path length correction member 112 and the dispersion compensation member 113, and is guided to the corner cube 114. The optical path length correction member 112 acts to match the optical path length of the reference light LR and the optical path length of the measurement light LS with each other. The dispersion compensation member 113 acts to match the dispersion characteristics of the reference light LR and the dispersion characteristics of the measurement light LS with each other. The corner cube 114 is movable along the incident direction of the reference light LR. With this, the optical path length of the reference light LR is changed.

The reference light LR that has passed through the corner cube 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the optical path length changing device 41, the optical scanner 42, the OCT focusing lens 43, the mirror 44, and the relay lens 45, and then reaches the dichroic mirror 46. The measurement light LS is reflected by the dichroic mirror 46, is refracted by the objective lens 22, and is incident on the subject's eye E. When applying OCT to the anterior eye segment Ea, the measurement light LS refracted by the objective lens 22 is further refracted by the lens group in the auxiliary lens unit 80 and is irradiated to the anterior eye segment Ea. The measurement light LS is reflected and scattered at various depth locations of the fundus Ef or those of the anterior eye segment Ea. The returning light of the measurement light LS from the subject's eye E travels along the same route as the outward way in the opposite direction, is directed to the fiber coupler 105, and then reaches the fiber coupler 122 via the optical fiber 128.

The fiber coupler 122 superposes (i.e., interferes) the measurement light LS incident through the optical fiber 128 and the reference light LR incident through the optical fiber 121 with each other, to generate interference light. The fiber coupler 122 splits the interference light at a predetermined splitting ratio (e.g., 1 to 1) to generate a pair of interference light LC. The pair of the interference light LC is guided to the detector 125 through the optical fibers 123 and 124, respectively.

The detector 125 is, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the DAQ 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, optically delays one of the two pieces of split light, generates the combined light of the two pieces of split light, and generates the clock KC based on the result of the detection of the combined light. The DAQ 130 performs the sampling of the detection signal input from the detector 125 based on the clock KC. The DAQ 130 sends the result of the sampling of the detection signal from the detector 125 to the arithmetic and control unit 200.

The present example is provided with both the optical path length changing device 41 for changing the length of the optical path of the measurement light LS (called the measurement optical path or the measurement arm) and the corner cube 114 for changing the length of the optical path of the reference light LR (called the reference optical path or the reference arm). However, only one of the optical path length changing device 41 and the corner cube 114 may be provided. An optical member other than these may be employed to change the difference between the measurement optical path length and the reference optical path length.

<Control System>

Figure 3A:
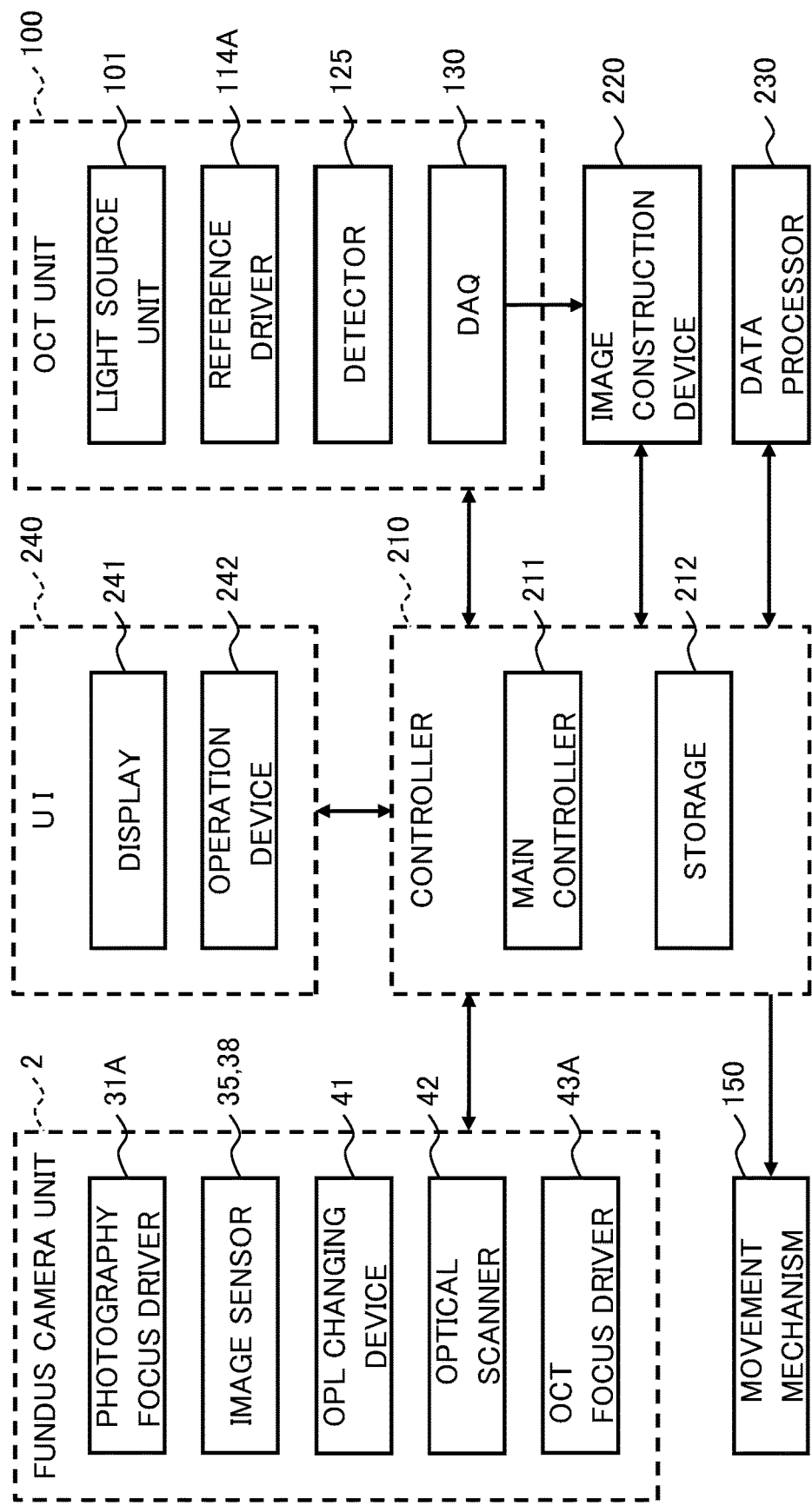
FIG. 3A is a schematic diagram illustrating an example of the configuration of the ophthalmologic apparatus according to the embodiment.
Figure 3B:
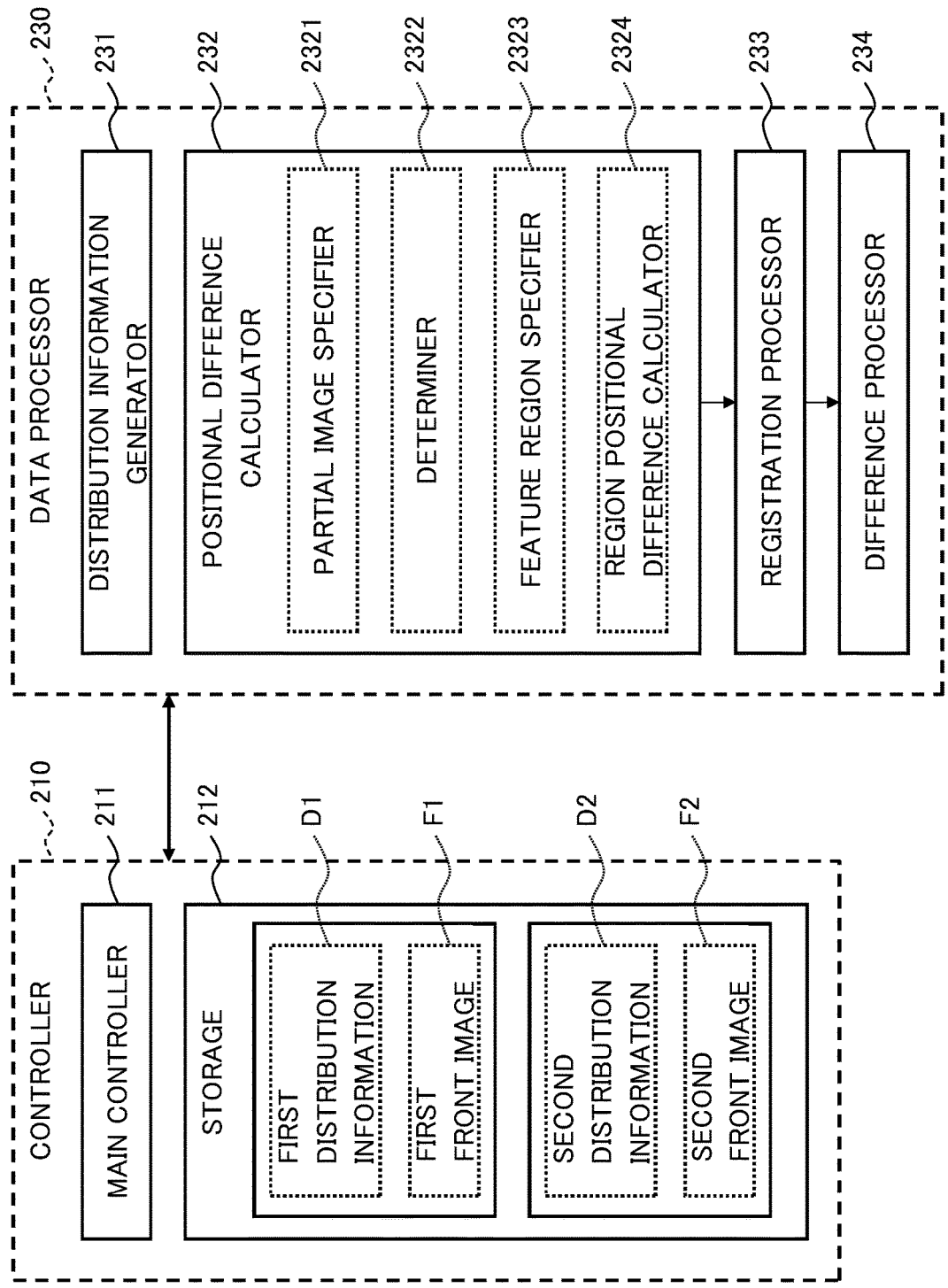
FIG. 3B is a schematic diagram illustrating an example of the configuration of the ophthalmologic apparatus according to the embodiment.

FIG. 3A and FIG. 3B show examples of the configuration of the control system of the ophthalmologic apparatus 1. The controller 210, the image construction device 220 and the data processor 230 are provided in the arithmetic and control unit 200.

<Controller 210>

The controller 210 performs various kinds of controls. The controller 210 includes the main controller 211 and the storage 212. The controller 210 includes one or more processors.

<Main Controller 211>

The main controller 211 controls each part of the ophthalmologic apparatus 1 (including the elements shown in FIG. 1 to FIG. 3B). Note that the photography focus driver 31A shown in FIG. 3A moves the photography focusing lens 31, the OCT focus driver 43A moves the OCT focusing lens 43, the reference driver 114A moves the corner cube 114, and the movement mechanism 150 moves the fundus camera unit 2 in a three dimensional manner.

<Storage 212>

The storage 212 stores various kinds of data. Examples of the data stored in the storage 212 include OCT images, anterior eye segment images, fundus images, and subject's eye information. The subject's eye information includes subject information such as the patient ID and the patient's name, identifiers for the left eye and the right eye, and electronic medical record information.

In the present embodiment, the storage 212 stores distribution information and front images. The distribution information is generated by analyzing data of the anterior eye segment Ea acquired using OCT. The distribution information represents a distribution of a predetermined parameter relating to the anterior eye segment Ea. The parameter (referred to as an anterior eye segment parameter) includes, for example, at least one of a parameter representing a corneal thickness (referred to as a corneal thickness parameter) and a parameter representing a corneal shape (referred to as a corneal shape parameter).

The corneal thickness parameter represents, for example, the thickness of one or more of the six layers of a cornea. A typical example of the corneal thickness parameter is the distance between the anterior corneal surface and the posterior corneal surface. The distance between the anterior and posterior corneal surfaces is the distance between the outer surface of the corneal epithelium and the inner surface of the corneal endothelium, which is regarded as the thickness of the whole corneal layer. An example of the distribution information on the corneal thickness parameter is a "corneal thickness map" that represents the distribution of the whole corneal layer thickness.

The corneal shape parameter represents, for example, the shape of the anterior surface of a cornea, the shape of the posterior surface of a cornea, the shape of a layer boundary, or the like. A typical example of the corneal shape parameter is corneal topography. The corneal topography is utilized for evaluation of the (three dimensional) shape of the anterior surface and/or the posterior surface of a cornea, and for acquisition of the refractive power distribution. The corneal topography is performed using a photokeratoscope, a videokeratoscope, a slit scan type corneal topographer, or the like.

A front image is, for example, an image acquired by photographing the anterior eye segment Ea from the front direction or from an oblique direction. An example of a means for photographing the anterior eye segment Ea from the front direction is the combination of the illumination optical system 10 and the photographing optical system 30 that are used for acquisition of observation images and photographed images of the anterior eye segment Ea. On the other hand, an example of a means for photographing the anterior eye segment Ea from an oblique direction is the anterior eye segment camera (at least one of two or more photographing devices) described in Japanese Unexamined Patent Application Publication No. 2013-248376. It is noted that the means for acquiring front images is not limited to these examples. For example, as described later, a front image may be reconstructed from data acquired using OCT.

In the present embodiment, OCT for acquiring the anterior eye segment parameter is performed a plurality of times in order to grasp the time-dependent change of the anterior eye segment Ea. For example, in preoperative and postoperative observation, OCT is performed respectively before and after surgery. In follow-up observation or prognosis management, the OCT is iteratively performed at regular intervals. In the present embodiment, a front image of the anterior eye segment Ea is acquired at the time of OCT being performed. The acquisition of a front image is performed, for example, at any timing in a period during which OCT is being performed. Alternatively, the acquisition of a front image may be carried out immediately before the start of OCT or immediately after the end of OCT. The timing at which the front image acquisition is performed may be any timing at which a front image, which substantially reflects the position of the subject's eye E at the time of OCT being performed, can be acquired.

In this way, OCT of the anterior eye segment Ea and the acquisition of a front image are performed in combination in the present embodiment. As will be described later, the data acquired by the OCT is used to generate distribution information representing a distribution of the anterior eye segment parameter. The distribution information generated is associated with the front image acquired in combination with the OCT of the anterior eye segment Ea, and stored in the storage 212. As shown in FIG. 3B, the first distribution information D1 acquired at a predetermined timing (the first time) and the first front image F1 acquired together with the first distribution information D1 are stored in association with each other. In addition, the second distribution information D2 acquired at a timing different from the first time and the second front image F2 acquired together with the second distribution information D2 are stored in association with each other.

Here, at least one of the first distribution information D1 and the second distribution information D2 may be generated by another apparatus. Further, a front image associated with the distribution information generated by another apparatus may also be an image acquired by another apparatus. For example, the controller 210 may acquire the first distribution information D1 and the first front image F1 acquired by another ophthalmologic apparatus from a database (e.g., a medical image archiving system) on the network, and store the first distribution information D1 and the first front image F1 acquired in the storage 212. Here, the another ophthalmologic apparatus may be an ophthalmologic apparatus installed in another medical facility. In addition, the ophthalmologic apparatus 1 of the present embodiment can process the second distribution information D2 and the second front image F2 acquired by the ophthalmologic apparatus 1 itself in combination with the first distribution information D1 and the first front image F1.

<Image Construction Device 220>

The image construction device 220 constructs an image based on the output from the DAQ 130 (that is, based on the sampling result of detection signals). For example, as in the conventional swept source OCT, the image construction device 220 applies signal processing to the spectral distribution formed from the sampling result for each A-line to form the reflection intensity profile for each A-line. Then, the image construction device 220 creates a plurality of pieces of image data from the reflection intensity profiles for a plurality of A-lines and arranges the plurality of pieces of image data along a scan line. The aforementioned signal processing includes noise elimination (or noise reduction), filtering, and fast Fourier transform (FFT), for example. The image construction device 220 includes one or more processors.

<Data Processor 230>

The data processor 230 applies image processing and/or analysis to the image constructed by the image construction device 220. For example, the data processor 230 executes construction of three dimensional image data (e.g., stack data, volume data) from raster scan data, rendering of three dimensional image data, image correction, image analysis according to analysis application software. The data processor 230 includes one or more processors. The data processor 230 includes the distribution information generator 231, the positional difference calculator 232, the registration processor 233, and the difference processor 234.

<Distribution Information Generator 231>

The distribution information generator 231 analyzes data acquired through OCT scanning of the anterior eye segment Ea to generate distribution information representing a distribution of the anterior eye segment parameter. This processing for generating the distribution information is executed using a known analysis application software (see, for example, Japanese Unexamined Patent Application Publication Translation of PCT Application) No. 2015-504740). As a typical example, when generating a corneal thickness map, the distribution information generator 231 performs segmentation of three dimensional data acquired by scanning a three dimensional region of the anterior eye segment Ea, to specify the image region corresponding to the anterior surface of the cornea and the image region corresponding to the posterior surface of the cornea, wherein the three dimensional region includes the cornea. The former image region is referred to as an anterior surface region, and the latter is referred to as a posterior surface region. Subsequently, the distribution information generator 231 calculates the distance between the anterior surface region and the posterior surface region for each of a plurality of positions, and then visualizes the distribution of the calculated distances to create a map.

<Positional Difference Calculator 232>

The positional difference calculator 232 calculates a positional difference (or, shift, displacement, or the like) between the first front image F1 and the second front image F2. This positional difference is the positional difference between an image depicted in the first front image F1 (anterior eye segment image) and an image depicted in the second front image F2. This positional difference corresponds to the difference between the position of the subject's eye E at the time of the first front image F1 being acquired and the position of the subject's eye E at the time of the second front image F2 being acquired.

When both the first front image F1 and the second front image F2 are acquired by the same device, the positional difference between the depicted images corresponds directly to the difference between the positions of the subject's eye E. On the other hand, when the first front image F1 and the second front image F2 are acquired by different devices from one another, a transformation between a coordinate system for one device and a coordinate system for another device is required. For example, suppose that the first front image F1 is acquired by photographing the anterior eye segment Ea from the front direction using the illumination optical system 10 and the photographing optical system 30. Meanwhile, suppose that the second front image F2 is acquired by photographing the anterior eye segment Ea from an oblique direction using the anterior eye segment camera described in Japanese Unexamined Patent Application Publication No. 2013-248376. In such a case, a coordinate transformation that takes the difference in the photographing direction (angle) into consideration is employed.

For example, the positional difference calculator 232 specifies the first region by analyzing the first front image F1 and specifies the second region corresponding to the first region by analyzing the second front image F2. Then, the positional difference calculator 232 calculates the positional difference between the first region and the second region. In such a series of processes, the positional difference calculator 232 can execute the followings, for example: specification of the first partial image in the first front image corresponding to at least one of the pupil and the iris; specification of the first region based on the first partial image specified; specification of the second partial image in the second front image corresponding to the at least one of the pupil and the iris as above; and specification of the second region based on the second partial image specified. In addition, the positional difference calculator 232 may be configured to specify any one or more of the followings for each of the first region and the second region: the region corresponding to the center of the pupil; the region corresponding to the center of gravity of the pupil; the region corresponding to the center of the iris; the region corresponding to the center of gravity of the iris; and the region representing the iris pattern.

In order to execute the exemplary processing described above, the positional difference calculator 232 according to the present example includes, for example, the partial image specifier 2321, the determiner 2322, the feature region specifier 2323, and the region positional difference calculator 2324. In other embodiments, a positional difference calculator including only some of these parts may be employed, or a positional difference calculator including an element different from any of these parts may be applied.

The partial image specifier 2321 specifies a partial image corresponding to a predetermined site of the anterior eye segment Ea by analyzing the first front image F1. The predetermined site is, for example, the pupil, the iris, or the pupil and the iris. Further, the process of specifying the partial image is executed based on the pixel values (e.g., brightness values) of the first front image F1. For example, the pupil is represented in the darkest tone in the anterior eye segment Ea. Further, the iris is represented in a brighter tone than that of the pupil and in a darker tone than that of the white of eye (i.e., the sclera, the conjunctiva). Therefore, the partial image specifier 2321 can acquire any one or more of the followings through binarization with a threshold value of brightness appropriately set: a partial image corresponding to the pupil (first pupil image); a partial image corresponding to the black part of eye, that is, the pupil and the iris (first black part image); and a partial image corresponding to the iris (first iris region of a ring-like shape). As for the second front image F2, the second pupil image, the second black part image, and the second iris image are acquired in the same manner. Since the edge of the black part image coincides with the outer edge of the iris image, the black part image and the iris image can be regarded as substantially the same as one another.

However, there are cases where the partial images cannot be acquired in a proper manner, or cases where the acquired partial images cannot be utilized in a proper manner. For example, changes in the pupil size (i.e., mydriasis, miosis) are not necessarily concentric. Therefore, in the case of determining the positional difference using the center of the pupil or the center of gravity of the pupil, an error occurs in the comparison of the positions of the center of the pupil or the center of gravity of the pupil if the size of the pupil image depicted in the first front image F1 is (greatly) different from the size of the pupil image depicted in the second front image F2. In addition, in the case where a front image is acquired with the eyelid not widely opened, the outer edge of the iris may not be depicted, or the eyelashes may be depicted in front of the iris, which makes it impossible to acquire an entire image of the iris and further makes it impossible to refer to the center of the iris or the center of gravity of the iris.

The determiner 2322 executes the determination whether such an unfavorable event has occurred. For example, when the partial image specifier 2321 specifies the first pupil image and the second pupil image, the determiner 2322 determines whether the first pupil image and the second pupil image satisfy a predetermined condition. The predetermined condition may be, for example, any of the followings: whether or not the difference between the size of the first pupil image and the size of the second pupil image is within a preset allowable range; and whether the size of the first pupil image and the size of the second pupil image are both within a preset allowable range. The parameter representing the sizes of pupil images may be any of the followings: the diameter of an approximate ellipse of the pupil image (e.g., major axis diameter, minor axis diameter, average diameter); the distance from the center of gravity of the pupil image to the edge (e.g., mean distance, maximum distance, minimum distance); the area (square measure) of the pupil image or of the approximate ellipse of the pupil image; and the circumference length of the pupil image (the length of the edge of the pupil image).

In addition, when the partial image specifier 2321 specifies the first iris image and the second iris image (including the case where the partial image specifier 2321 specifies the first black part image and the second black part image), the determiner 2322 determines whether the first iris image and the second iris image satisfy a predetermined condition (or, whether the first black part image and the second black part image satisfy a predetermined condition). The predetermined condition may be, for example, any of the followings: whether or not the entire outer edge of the iris is depicted; and to what extent the part not depicted due to eyelashes etc. exists.

The feature region specifier 2323 specifies a feature region corresponding to a feature site of the anterior eye segment Ea based on the partial images specified by the partial image specifier 2321. The feature region may be, for example, any one or more of the followings as described above: a region corresponding to the center of the pupil (pupil center region); a region corresponding to the center of gravity of the pupil (pupil gravity center region); a region corresponding to the center of the iris (iris center region); a region corresponding to the center of gravity of the iris (iris gravity center region); and a region representing the iris pattern (iris pattern region).

The determination of the pupil center region includes, for example, a process of determining an approximate ellipse of the pupil image obtained as a partial image, and a process of determining the center of the approximate ellipse. Likewise, the determination of the iris center region includes, for example, a process of determining an approximate ellipse of the iris image, and a process of determining the center of the approximate ellipse. The process of determining the pupil gravity center region or the iris gravity center region is executed, for example, using a known arithmetic formula $((x_1+x_2+\ldots+x_n)/n, (y_1+y_2+\ldots+y_n)/n)$ for determining the center of gravity of an image region consisting of n pixels $P_i$ $(x_i, y_i)$ (where i=1 to n). The process of determining the iris pattern region is performed by applying any pattern recognition technique (e.g., a well-known Daugman algorithm) utilized for known iris recognition. The process of determining the iris pattern region includes, for example, a wavelet transformation with a Gabor filter, and extraction of phase information from the information obtained by the wavelet transformation. It is noted that a feature region and a process for specifying the feature region are not limited to the above examples.

The region positional difference calculator 2324 calculates the positional difference between the feature region in the first front image F1 and the feature region in the second front image F2 specified by the feature region specifier 2323, as the positional difference between the first front image F1 and the second front image F2. Here, the feature region in the first front image F1 and the feature region in the second front image F2 are image regions both corresponding to the same feature site of the anterior eye segment Ea. For example, the region positional difference calculator 2324 calculates the direction and amount of the difference between the position of the pupil center region in the first front image F1 and the position of the pupil center region in the second front image F2.

The region positional difference calculator 2324 may be configured to perform magnification adjustment between the first front image F1 and the second front image F2. The magnification adjustment is carried out, for example, when the photographing magnification of the first front image F1 and the photographing magnification of the second front image F2 are different from each other. In the event where the photographing magnifications of the first front image F1 and the second front image F2 are known, for example, the magnification adjustment may be performed based on the ratio between the photographing magnifications. Further, the magnification adjustment may be carried out by means of any of the followings: comparison between the sizes of one or more landmarks in the first front image F1 and the sizes of one or more landmarks in the second front image F2; comparison between the positional relationship (e.g., distance, location) between two or more landmarks in the first front image F1 and the positional relationship between two or more landmarks in the second front image F2. The amount of the rotational positional difference and the amount of the parallel movement between the first front image F1 and the second front image F2 may be determined in a similar manner. The above processing can be executed, for example, as a process of determining an affine transformation matrix between the first front image F1 and the second front image F2.

In addition to the calculation of the positional difference between the first front image F1 and the second front image F2, the positional difference calculator 232 may perform image matching (i.e., image registration) between the first front image F1 and the second front image F2. The image matching is a process of relatively moving the first front image F1 and the second front image F2 (in a single coordinate system) so that the positional difference calculated is cancelled.

<Registration Processor 233>

The registration processor 233 applies registration to the first distribution information D1 and the second distribution information D2 according to the positional difference between the first front image F1 and the second front image F2 obtained by the positional difference calculator 232.

The first front image F1 is an image acquired during or immediately before or immediately after the first data used for generating the first distribution information D1 is acquired. Further, the second front image F2 is an image acquired during or immediately before or immediately after the second data used for generating the second distribution information D2 is acquired. Therefore, the positional difference between the first front image F1 and the second front image F2 is substantially equal to the difference between the position of the subject's eye E at the time of the first data being acquired and the position of the subject's eye E at the time of the second data being acquired, and thus substantially equal to the positional difference between the first distribution information D1 and the second distribution information D2.

Using such a relationship, the registration processor 233 carries out registration between the first distribution information D1 and the second distribution information D2 by relatively moving the first distribution information D1 and the second distribution information D2 so as to cancel the positional difference between the first front image F1 and the second front image F2. With this, for example, position matching between the first distribution information D1 and the second distribution information D2 is achieved in such a manner that the position corresponding to the center of the pupil in the first distribution information D1 matches the position corresponding to the center of the pupil in the second distribution information D2.

Note that some embodiments do not require actual performance of position adjustment (position matching) between the first distribution information D1 and the second distribution information D2, and only requires to obtain association (or, correspondence or relationship) between a set of positions in the first distribution information D1 (e.g., a set of values of the anterior eye segment parameter) and a set of positions in the second distribution information D2 (e.g., a set of values of the anterior eye segment parameter). Here, when the number of elements of the set corresponding to the first distribution information D1 is equal to the number of elements of the set corresponding to the second distribution information D2, a "one-to-one" association (or correspondence) is made between these sets. In other words, such association is made as a bijection from one distribution information to the other distribution information.

On the other hand, when the number of elements of the set corresponding to the first distribution information D1 is different from the number of elements of the set corresponding to the second distribution information D2, to each of the elements of one set having smaller number of elements, one element of the other set is assigned. In other words, this association is made as an injection from the distribution information having a smaller number of elements into the distribution information having a larger number of elements. If two or more elements of the distribution information having a larger number of elements can be assigned to a single element of the distribution information having a smaller number of elements, a statistical value (e.g., average value) derived from the values represented by the two or more elements (e.g., the values of the anterior eye segment parameter) may be assigned to the single element.

<Difference Processor 234>

The difference processor 234 obtains difference information representing difference between the first distribution information D1 and the second distribution information D2 to which the registration has been applied by the registration processor 233. As described above, the registration processor 233 makes an association between the set of values of the anterior eye segment parameter included in the first distribution information D1 and the set of values of the anterior eye segment parameter included in the second distribution information D2. The difference processor 234 determines the difference between a pair of values of the anterior eye segment parameter associated with one another. For example, the difference processor 234 subtracts, from each of the values of the anterior eye segment parameter included in the first distribution information D1, its corresponding value included in the second distribution information D2. When a corneal thickness map, which is a typical specific example, is used, for example, a map (a difference map), which represents the distribution of the amount of change between the latest corneal thickness map and the corneal thickness map acquired in the previous examination, is obtained. Here, a corneal thickness map used to be a baseline in follow-up observation may be employed in place of the corneal thickness map acquired in the previous examination.

<User Interface 240>

The user interface 240 includes the display 241 and the operation device 242. The display 241 includes the display device 3. The operation device 242 includes various kinds of operation devices and input devices. The user interface 240 may include a device, such as a touch panel, that has both the display function and the operation function. It is also possible to construct an embodiment that does not include at least part of the user interface 240. For example, the display device may be an external device connected to the ophthalmologic apparatus.

<Operation>

Figure 4:
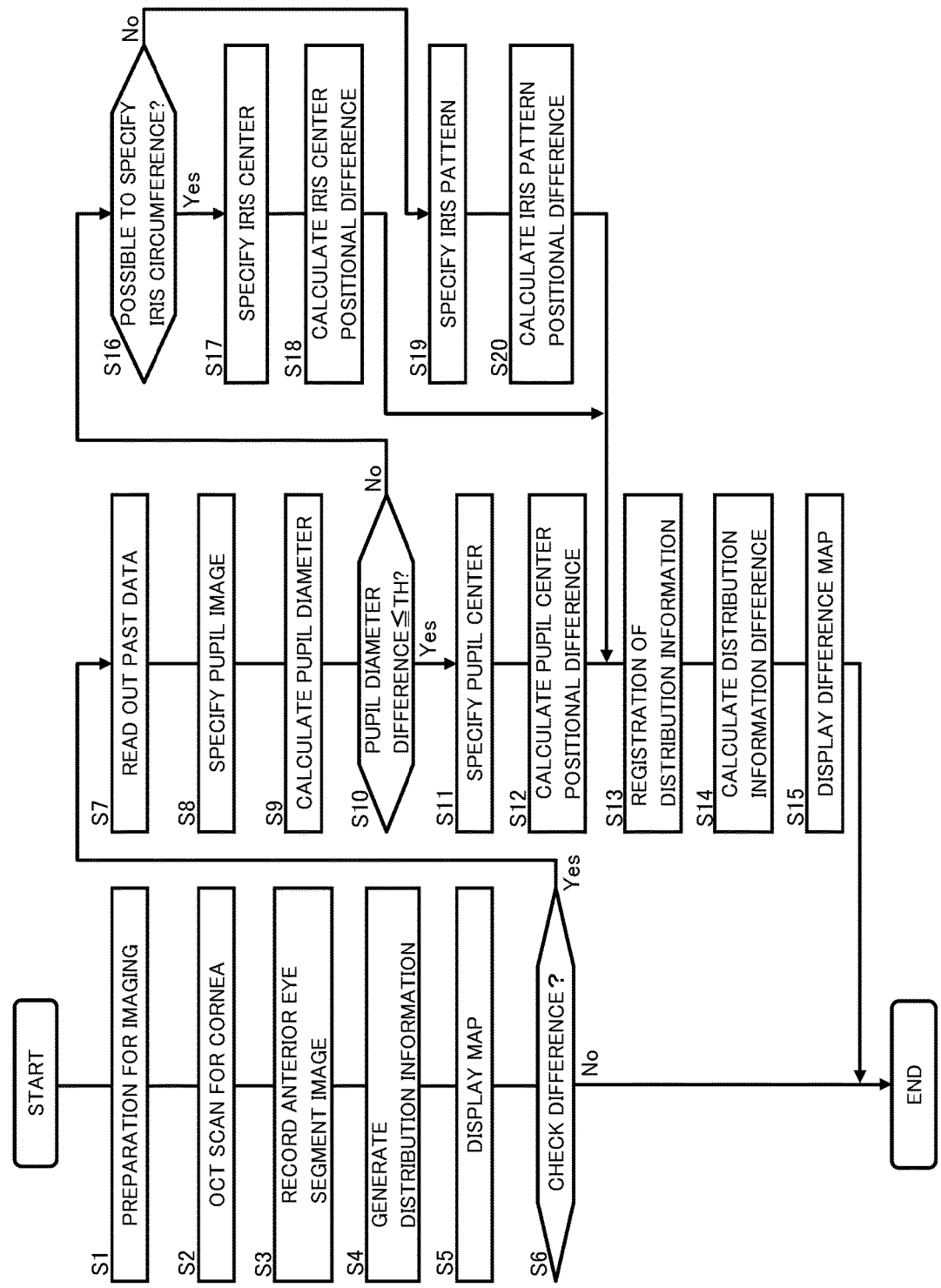
FIG. 4 is a flowchart illustrating an example of the operation of the ophthalmologic apparatus according to the embodiment.

The operation of the ophthalmologic apparatus 1 will be described. An example of the operation is shown in FIG. 4.

(S1: Preparation for Imaging)

First, preparatory operations for imaging are performed. The examiner activates the ophthalmologic apparatus 1 and selects a desired measurement mode (e.g., corneal thickness measurement mode). Then, the examiner uses the operation device 242 (e.g., a joystick) to move the main body of the apparatus (e.g., the fundus camera unit 2) away from the chin rest etc. Further, the auxiliary lens unit 80 for applying OCT to the anterior eye segment Ea is inserted into the optical path. With this, observation, imaging and OCT can be applied to the anterior eye segment Ea.

The subject is seated on a chair (not illustrated), the chin is placed on the chin rest, and the forehead is brought into contact with the forehead rest. The examiner adjusts the height of the chin rest etc. according to the sitting height of the subject. Upon receiving a predetermined operation, the main controller 211 turns on the observation light source 11 and the LED 51, and displays an observation image (an anterior eye segment observation image) based on the outputs from the image sensor 35 on the display 241. Two alignment bright spot images are depicted in the observation image. The examiner (or the ophthalmologic apparatus 1) adjusts the position of the main body of the apparatus in such a manner that the two alignment bright spot images overlap with each other and are depicted within a target area (defined by brackets, for example) displayed at the center of the frames.

The main controller 211 controls the focus optical system 60 to project the split indicator. The examiner (or the ophthalmologic apparatus 1) performs the optical path length adjustment (e.g., the adjustment of at least one of the position of the optical path length changing device 41 and the position of the corner cube 114), the polarization adjustment (e.g., the control of at least one of the polarization controllers 103 and 118), the light amount adjustment (e.g., the control of the attenuator 120), the focus adjustment (e.g., the adjustment of the position of the OCT focusing lens 43), and other adjustments.

After the completion of the series of preparatory processes as described above, the examiner (or the ophthalmologic apparatus 1) checks whether or not problems such as flare mixing have occurred in the observation image. When it has been confirmed that no problem has occurred, the examiner performs an operation to start imaging (imaging start trigger operation) using the operation device 242. Upon receiving the start of imaging issued by the examiner, the main controller 211 can overlay an image that represents the current scan position by OCT on the observation image.

(S2: OCT Scan for Cornea)

In response to the aforementioned imaging start trigger operation, the main controller 211 controls the OCT unit 100 and the optical scanner 42 to apply OCT scanning to the anterior eye segment Ea. With the OCT scanning, a three dimensional region in anterior eye segment Ea, which includes at least part of the cornea, is scanned.

(S3: Record Anterior Eye Segment Image)

As described above, the acquisition of the anterior eye segment observation image started in step S1 is being continued at this stage. The main controller 211 saves a frame acquired in a period during (or immediately before or immediately after) the OCT scanning in step S2 is being performed, in the storage 212 as a front image. The front image (anterior eye segment image) is treated as the second front image F2 shown in FIG. 3B. At this stage, the first distribution information D1, the first front image F1, and the second distribution information D2 are not yet stored in the storage 212.

If it has been specified in step S1 that check of difference (e.g., follow-up observation, preoperative and postoperative observation, etc.) is to be performed, the ophthalmologic apparatus 1 may acquire past data (e.g., the first distribution information D1, the first front image F1) from the medical image archiving system, an electronic medical record system, etc. at any stage so far. The ophthalmologic apparatus 1 acquires the past data by, for example, transmitting a data transmission request including the subject identifier to the medical image archiving system or the like and receiving the past data transmitted in response to the request. In the example shown in FIG. 4, the selection whether or not checking of difference is necessary is carried out in step 6.

(S4: Generate Distribution Information)

The distribution information generator 231 generates distribution information such as a corneal thickness map, based on the data acquired by the OCT scanning in step S2. The distribution information generated is stored in the storage 212 as the second distribution information D2.

(S5: Display Map)

The main controller 211 displays the map representing the second distribution information D2 generated in step S4 on the display 241. At this time, the map may be overlaid on the second front image F2, or the map is displayed side by side with the second front image F2.

(S6: Check Difference?)

If desiring to check the difference between the distribution information acquired in the past examination and the distribution information acquired this time, the examiner performs a predetermined operation (S6: Yes). If this is the case, the process proceeds to step S7.

On the other hand, if check of difference is not performed (S6: No), the examiner carries out an operation to end the examination. The main controller 211 transmits the second distribution information D2 and the second front image F2 acquired this time, together with the subject identifier etc., to the medical image archiving system or the like. The medical image archiving system stores the subject identifier, the second distribution information D2, the second front image F2, the examination date and time, etc. in association with each other.

(S7: Read Out Past Data)

In the event where the examiner has performed the operation for checking the difference in step S6 (S6: Yes), the main controller 211 reads out the past data from the medical image archiving system or the like in the manner as described above. The main controller 211 stores the past data read out, in the storage 212 as the first distribution information D1 and the first front image F1.

(S8: Specify Pupil Image)

The partial image specifier 2321 specifies a pupil image (the first pupil image) in the first front image F1. Further, the partial image specifier 2321 specifies a pupil image (the second pupil image) in the second front image F2.

(S9: Calculate Pupil Diameter)

The determiner 2322 calculates the diameter (the first pupil diameter) of the first pupil image specified in step S8 and calculates the diameter of the second pupil image (the second pupil diameter). The process of calculating the pupil diameter includes, for example, the following processes: a process of determining an approximate ellipse (or an approximate circle) of the circumference of a pupil image; and a process of determining the diameter (i.e., major axis, minor axis, a diameter in a predetermined direction, an average value of diameters in a plurality of directions) of the approximate ellipse.

(S10: Is Pupil Diameter Difference Equal to or Less than Threshold Value?)

The determiner 2322 determines whether the difference between the first pupil diameter and the second pupil diameter calculated in step S9 is equal to or less than a threshold value. When the determiner 2322 determines that the difference is equal to or less than the threshold value (S10: Yes), the process proceeds to step S11. On the other hand, when the determiner 2322 determines that the difference is not equal to or less than the threshold value (S10: No), the process proceeds to step S16.

(S11: Specify Pupil Center)

When the determiner 2322 has determined in step S10 that the difference between the first pupil diameter and the second pupil diameter is equal to or less than the threshold value (S10: Yes), the feature region specifier 2323 specifies the center of the first pupil image (the first pupil center) and the center of the second pupil image (the second pupil center). The process of specifying the center of the pupils includes, for example, a process of determining an approximate ellipse (or an approximate circle) of the circumference of the pupil image; and a process of specifying the center of the approximate ellipse.

(S12: Calculate Positional Difference of Pupil Centers)

The region positional difference calculator 2324 calculates the positional difference between the first pupil center and the second pupil center specified in step S11. The positional difference calculated is used as the positional difference between the first front image F1 and the second front image F2.

(S13: Registration of Distribution Information)

The registration processor 233 applies registration to the first distribution information D1 and the second distribution information D2 based on the positional difference calculated in step S12.

(S14: Calculate Difference of Distribution Information)

The difference processor 234 calculates the difference between the first distribution information D1 and the second distribution information D2 to which the registration has been applied in step S13.

(S15: Display Difference Map)

The main controller 211 displays a difference map representing the differences calculated for the respective positions in step S14 on the display 241. At this time, the main controller 211 can overlay the difference map on the second front image F2 (or on the first front image F1), or display the difference map side by side with the second front image F2 (and/or with the first front image F1). With the above, the process in this case is completed.

(S16: Is it Possible to Specify Circumference of Iris?)

When the determiner 2322 has determined in step S10 that the difference between the first pupil diameter and the second pupil diameter is not equal to or less than the threshold value (S10: No), the partial image specifier 2321 specifies an iris image (the first iris image) in the first front image F1. Further, the partial image specifier 2321 specifies an iris image (the second iris image) in the second front image F2. Note that black part images may be obtained in place of the iris images. The feature region specifier 2323 specifies an outer edge region of the first iris image and specifies an outer edge region of the second iris image.

The determiner 2322 calculates the degree of similarity between the outer edge region and an ellipse (or a circle). This process includes, for example, the following processes: a process of calculating the area difference, the area ratio, the circumference length difference, or the circumference length ratio, between the outer edge region and its approximate ellipse; and a process of determining whether the area difference etc. calculated is equal to or less than a predetermined threshold value. When the area difference etc. is equal to or less than the threshold value, the determiner 2322 determines that the degree of similarity between the outer edge region and the ellipse is high, and that the entire circumference of the iris has been specified. When the determiner 2322 determines that the entire circumference of the iris has been specified for the first iris image and the entire circumference of the iris has been specified for the second iris image, it is determined "Yes" in step S16. In this case, the process proceeds to step S17.

On the other hand, when the area difference etc. is not equal to or less than the threshold value, the determiner 2322 determines that the degree of similarity between the outer edge region and the ellipse is low, and the entire circumference of the iris has not been specified. This case occurs, for example, when the eyelids are not sufficiently opened and the outer edge of the iris is hidden or when the eyelashes are covering over part of the iris. When the determiner 2322 determines that the entire circumference of the iris has not been specified for at least one of the first iris image and the second iris image, it is determined "No" in step S16. In this case, the process proceeds to step S19.

(S17: Specify Iris Center)

When the determiner 2322 has determined "Yes" in step S16, the feature region specifier 2323 specifies the center of the first iris image (the first iris center) and the center of the second iris image (the second iris center). The process of specifying the center of the iris is executed in the same manner as the process of determining the center of the pupil.

(S18: Calculate Positional Difference of Iris Centers)

The region positional difference calculator 2324 calculates the positional difference between the first iris center and the second iris center specified in step S17. The positional difference calculated is used as a positional difference between the first front image F1 and the second front image F2. Then, the process proceeds to step S13.

In step S13, the registration processor 233 applies registration to the first distribution information D1 and the second distribution information D2 based on the positional difference calculated in step S18. In step S14, the difference processor 234 calculates the difference between the first distribution information D1 and the second distribution information D2 to which the registration has been applied in step S13. In step S15, the main controller 211 displays a difference map representing the differences calculated for the respective positions in step S14 on the display 241. With the above, the process in this case is completed.

(S19: Specify Iris Pattern)

When the determiner 2322 has determined "No" in step S16, the feature region specifier 2323 specifies an iris pattern region in the first iris image (the first iris pattern region) and an iris pattern region in the second iris image (the second iris pattern region). The process of specifying the iris pattern regions is executed in the same manner as described above.

(S20: Calculate Positional Difference of Iris Patterns)

The region positional difference calculator 2324 calculates the positional difference between the first iris pattern region and the second iris pattern region specified in step S19. The positional difference calculated is used as a positional difference between the first front image F1 and the second front image F2. By comparing the iris pattern regions, in addition to the positional difference in the xy plane, inclination (gradient) due to eye rotation etc. can be detected. Then, the process proceeds to step S13.

In step S13, the registration processor 233 applies registration to the first distribution information D1 and the second distribution information D2 based on the positional difference calculated in step S20. In addition to the registration in the xy direction as with the other cases, the registration may include correction of the inclination described above. In step S14, the difference processor 234 calculates the difference between the first distribution information D1 and the second distribution information D2 to which the registration has been applied in step S13. In step S15, the main controller 211 displays a difference map representing the differences calculated for the respective positions in step S14 on the display 241. The process in this case is completed with the above.

MODIFICATION EXAMPLES

Some modification examples of the above embodiment will be described. In the following modification examples, the same reference symbols are given to the same or similar elements as or to those in the above embodiment.

Modification Example 1

Figure 5:
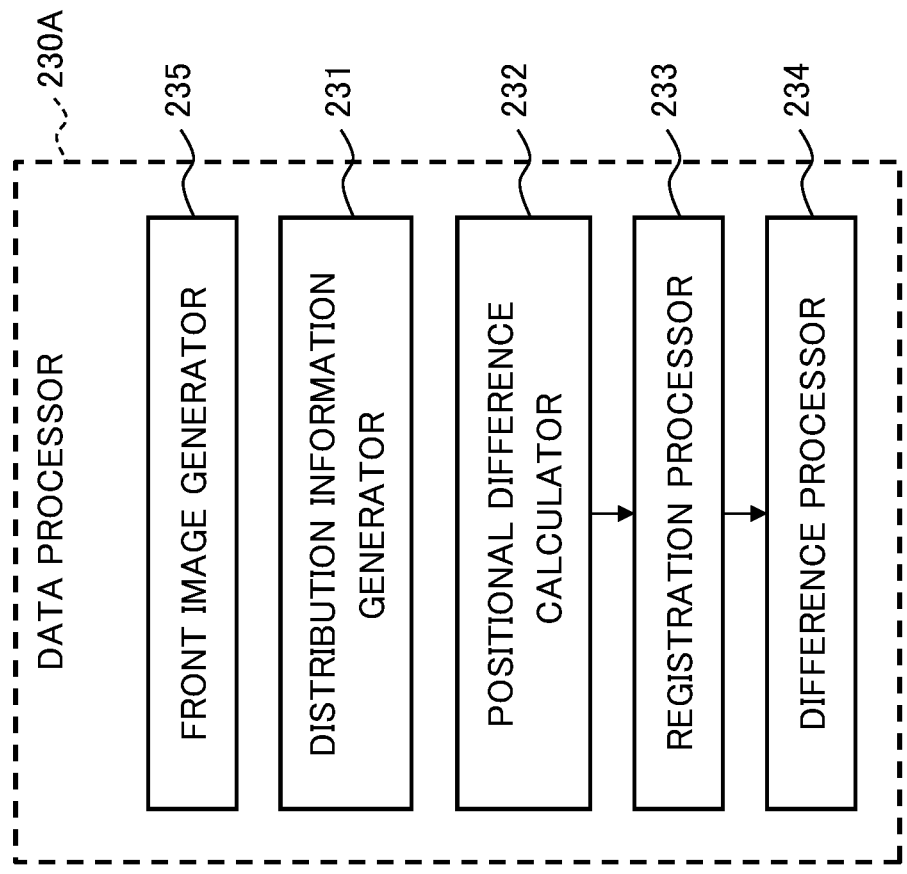
FIG. 5 is a schematic diagram illustrating an example of the configuration of the ophthalmologic apparatus according to the modification example.

The above embodiment is configured to acquire front images by photographing the anterior eye segment Ea from the front direction or an oblique direction. The method of acquiring front images is not limited to these. For example, a front image may be generated based on three dimensional data acquired by scanning a three dimensional region of the anterior eye segment Ea. FIG. 5 shows an example of the configuration for that purpose. The data processor 230A shown in FIG. 5 may be employed in place of the data processor 230 in the above embodiment.

The data processor 230A includes the front image generator 235, in addition to the distribution information generator 231, the positional difference calculator 232, the registration processor 233, and the difference processor 234 like the above embodiment. The front image generator 235 may be configured to generate a front image (i.e., a projection image) by projecting entire three dimensional data acquired by scanning a three dimensional region of the anterior eye segment Ea in the z direction. The front image generator 235 may be configured to generate a front images (i.e., a shadowgram) by projecting part of the three dimensional data in the z direction. The front image generator 235 may be configured to generate a front images (i.e., a C-scan image) from a desired xy cross section of the three dimensional data. The front image generator 235 may be configured to apply segmentation to the three dimensional data to specify an image region corresponding to a desired tissue (e.g., corneal epithelium, corneal endothelium, or the like), and convert the specified image region to a planar image to generate a front image (i.e. a flattened image). The processes described above are merely typical examples for generating a front image from three dimensional data and any other processes or methods may be employed.

Modification Example 2

As described above, it is generally not appropriate to determine a positional difference between the first front image and the second front image with the center of the pupil or the center of gravity of the pupil as a reference in the case where the pupil size when the first front image (the first distribution information) is acquired is significantly different from the pupil size when the second front image (the second distribution information) is acquired. Therefore, the above embodiment perform pupil size determination after OCT scanning. On the other hand, the present modification executes pupil size adjustment as preparation for OCT scanning.

Figure 6:
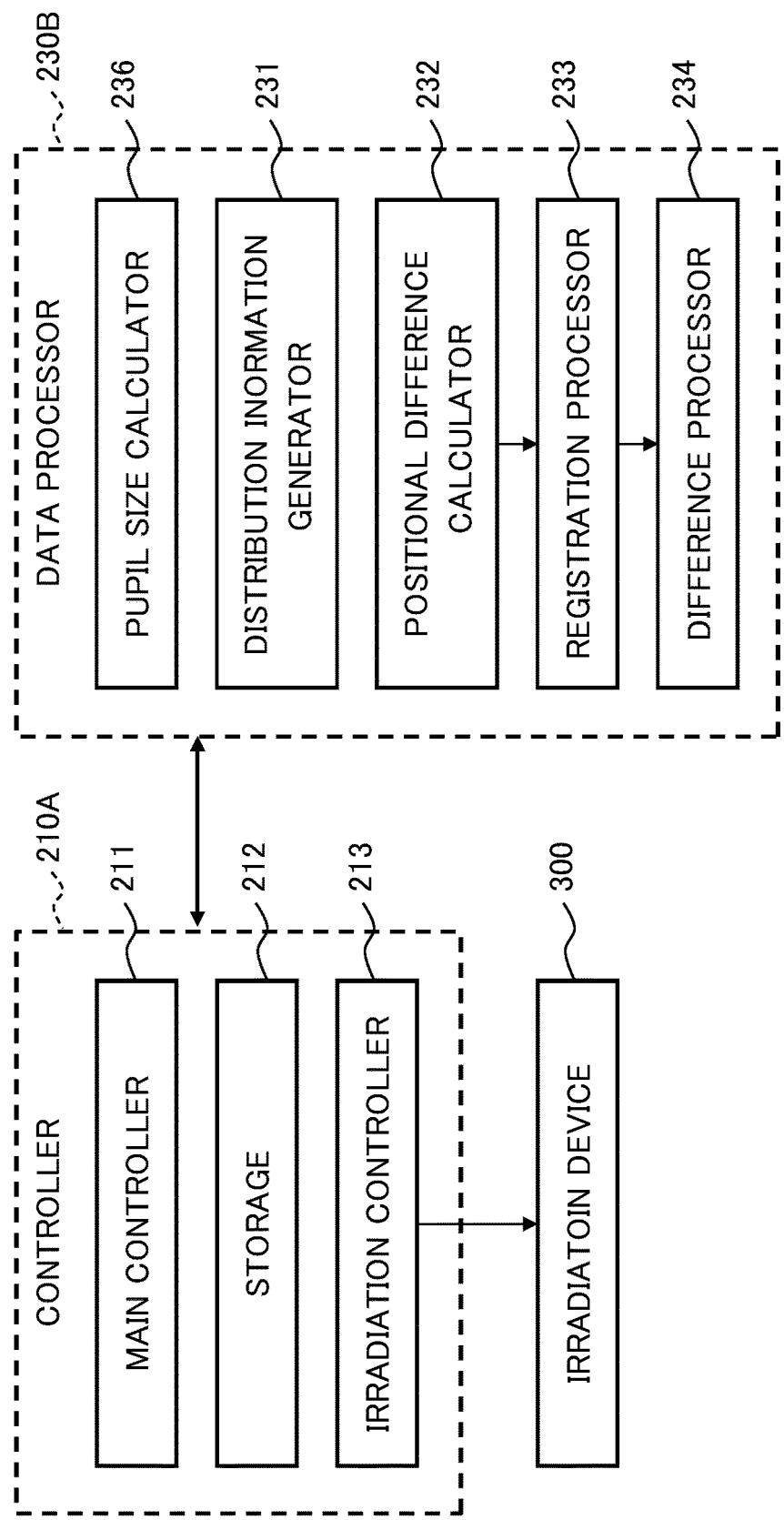
FIG. 6 is a schematic diagram illustrating an example of the configuration of the ophthalmologic apparatus according to the modification example.

An example of the configuration for that purpose is shown in FIG. 6. The controller 210A shown in FIG. 6 is provided in place of the controller 210 of the above embodiment, and the data processor 230B is employed in place of the data processor 230. The controller 210A is provided with the irradiation controller 213 in addition to the main controller 211 and the storage 212 as with those in the above embodiment. The irradiation controller 213 may be provided in the main controller 211. The data processor 230B includes the pupil size calculator 236 in addition to the distribution information generator 231, the positional difference calculator 232, the registration processor 233, and the difference processor 234 as with those in the above embodiment. Furthermore, the ophthalmologic apparatus according to the present modification includes the irradiation device 300.

The irradiation device 300 irradiates visible light to the subject's eye E. The irradiation device 300 may, for example, include the illumination optical system 10. The irradiation device 300 may include a light source (and an optical system) different from the illumination optical system 10. The irradiation controller 213 controls the irradiation device 300. The control of the irradiation controller 213 includes at least on and off control of visible light irradiation, and may further include a control of changing the light amount (intensity) of visible light irradiation.

The pupil size calculator 236 calculates a value representing the size of the pupil image in the same manner as in the above embodiment, for example. A typical example of this value is a pupil diameter.

When the first front image F1 (and the first distribution information D1) has already been acquired and the second front image F2 has not yet been acquired, that is, when carrying out examination for acquiring the second front image F2 (and the second distribution information D2), the positional difference calculator 232 (the partial image specifier 2321) specifies a pupil image (the first pupil image) in the first front image F1. The pupil size calculator 236 calculates a value representing the size of the first pupil image (e.g., the pupil diameter). The irradiation controller 213 controls the irradiation device 300 to output visible light having the intensity corresponding to the pupil diameter or the like calculated. The visible light may be continuous light or flash light. The intensity of the visible light corresponding to the pupil diameter or the like is determined, for example, by referring to predetermined information (e.g., a table, a graph) that shows correspondence between pupil diameters or the like and intensities of visible light. Alternatively, the ophthalmologic apparatus according to the present modification may be configured to irradiate visible light while acquiring an observation image of the anterior eye segment Ea, monitor the pupil size in the frames sequentially captured, and execute feedback control of the intensity of the visible light.

In this way, the present modification example is capable of making the pupil size at the time of OCT scanning and the pupil size at the time of front image acquisition (approximately) equal. Therefore, registration can be applied to distribution information with reference to the center of the pupil, the center of gravity of the pupil, or the like.

Modification Example 3

As in the modification example 2, the present modification provides an example for executing pupil size adjustment as preparation for OCT scanning. The configuration for that purpose may be the same as or similar to that of the modification example 2 (see FIG. 6).

In the present modification, a front image of the anterior eye segment Ea is acquired before OCT scanning of the anterior eye segment Ea to acquire data. The positional difference calculator 232 (the partial image specifier 2321) specifies a pupil image in the front image acquired. The pupil size calculator 236 calculates a value representing the size of the pupil image (e.g., the pupil diameter). The irradiation controller 213 (or the determiner 2322) determines whether the pupil diameter or the like calculated is equal to or less than a predetermined threshold value. When it is determined that the pupil diameter or the like is equal to or less than the threshold value, the irradiation controller 213 controls the irradiation device 300 to output visible light. In this manner, OCT scanning and front image acquisition are performed after the pupil of the subject's eye has become smaller (after miosis has occurred).

In the present modification, an iris image in a front image tend to become large and thus iris pattern recognition becomes easier. Taking into account this fact, the positional difference calculator 232 (the feature region specifier 2323) may be configured to specify an iris pattern region and calculate the positional difference between the first front image F1 and the second front image F2 based on the iris pattern region specified.

Actions and Effects

The actions and effects of ophthalmologic apparatuses according to some embodiments or modification examples will be described.

The ophthalmologic apparatus of some embodiments includes a data acquisition device, a distribution information generator, a front image acquisition device, a storage, a positional difference calculator, and a registration processor.

The data acquisition device is configured to acquire data by scanning an anterior eye segment of a subject's eye using optical coherence tomography technique. In the above example, the data acquisition device includes elements in the OCT unit 100 and elements in the fundus camera unit 2 that forms an optical path of the measurement light LS.

The distribution information generator is configured to generate distribution information representing a distribution of a predetermined parameter (an anterior eye segment parameter) in the anterior eye segment by analyzing the data acquired. In the above example, the distribution information generator includes the distribution information generator 231.

The front image acquisition device is configured to acquire a front image of the anterior eye segment at the time of the data being acquired by the data acquisition device. In the above example, the front image acquisition device includes a combination of the illumination optical system 10 and the imaging optical system 300, or an anterior eye segment camera that photographs the anterior eye segment Ea from an oblique direction. Alternatively, the front image acquisition device includes one or more processors that generate a front image from three dimensional data acquired by the data acquisition device. An example of such a processor is the front image generator 235 in the modification described above.

The storage is configured to store the first distribution information (D1) generated from the first data acquired at the first time, the first front image (F1) acquired at the time of the first data being acquired, the second distribution information (D2) generated from the second data acquired at the second time, and the second front image (F2) acquired at the time of the second data being acquired. In the above example, the storage includes the storage 212. It is noted that part of the distribution information and/or part of the front image stored in the storage may be acquired by another ophthalmologic apparatus.

The positional difference calculator is configured to calculate the positional difference between the first front image (F1) and the second front image (F2). In the above example, the positional difference calculator includes the positional difference calculator 232.

The registration processor is configured to apply registration to the first distribution information (D1) and the second distribution information (D2) based on the positional difference calculated by the positional difference calculator. In the above example, the registration processor includes the registration processor 233.

The ophthalmologic apparatus thus configured can utilize the front images acquired substantially at the same time as OCT scanning to execute registration of distribution information. This makes it possible for the examiner to accurately grasp the time-dependent change in anterior eye segment parameters irrespective of the presence or absence, or degree of the shape change of the cornea. Therefore, the ophthalmologic apparatus can be effectively used for comparative observation before and after surgery or the like.

In some embodiments, the positional difference calculator may include a region specifier and a region positional difference calculator. The region specifier is configured to specify the first region by analyzing the first front image (F1). Further, the region specifier is configured to specify the second region corresponding to the first region by analyzing the second front image (F2). The first region may correspond to any tissue of the anterior eye segment or any artificial object. Examples of the artificial object include a refractive correction implement such as an intraocular lens. Other examples of the artificial object include an instrument, a marker, and a stamp used for surgery. The marker is, for example, a pattern of light projected onto the anterior eye segment Ea. The region positional difference calculator is configured to calculate the positional difference between the first region and the second region as the positional difference between the first front image (F1) and the second front image (F2). In the above example, the region specifer includes the partial image specifier 2321 and the feature region specifier 2323. In addition, the region positional difference calculator includes the region positional difference calculator 2324.

In some embodiments, the region specifier may be configured to specify the first partial image in the first front image corresponding to at least one of the pupil and the iris, and specify the first region based on the first partial image. Likewise, the region specifier may be configured to specify the second partial image in the second front image corresponding to the at least one of the pupil and the iris, and specify the second region based on the second partial image. In the above example, the first partial image and the second partial image are the pupil images, the iris images, the black part images, or like images.

In some embodiments, the region specifier may be configured to specify any one or more of the followings for each of the first region and the second region: a region corresponding to the center of the pupil; a region corresponding to the center of gravity of the pupil; a region corresponding to the center of the iris; a region corresponding to the center of gravity of the iris; and a region representing the iris pattern.

In some embodiments, the region specifier may be configured to specify the first pupil image corresponding to the pupil as the first partial image and the second pupil image corresponding to the pupil as the second partial image. If this is the case, the ophthalmologic apparatus of some embodiments may further include the first determiner that determines whether the first pupil image and the second pupil image satisfy a predetermined condition. The condition may be, for example, any one of the followings: a condition that the difference between the size of the first pupil image and the size of the second pupil image is within a predetermined allowable range; and a condition that the size of the first pupil image and the size of the second pupil image both are within a predetermined allowable range. In the above example, the first determiner includes the determiner 2322.

The region positional difference calculator may be configured to calculate the positional difference between the first region and the second region based on regions corresponding to the center of the pupil or the center of gravity of the pupil in the event that the first determiner determines that the predetermined condition is satisfied. In addition, registration can be applied to the first distribution information and the second distribution information according to the positional difference calculated here. With such a configuration, the ophthalmologic apparatus can execute registration of distribution information with reference to the center of the pupil or the center of gravity of the pupil in the case where a good pupil image has been acquired.

On the other hand, when the first determiner determines that the predetermined condition is not satisfied, the region specifier may specify the first iris image corresponding to the iris as the first partial image and the second iris image corresponding to the iris as the second partial image. With such a configuration, the ophthalmologic apparatus can automatically proceed to a process using the iris images, in the case where a good pupil image has not been acquired.

The ophthalmologic apparatus of some embodiments may further include, for the case where a good pupil image has not been acquired, a second determiner that determines whether the first iris image and the second iris image satisfy a predetermined condition. The condition here is, for example, that the entire circumference of the iris is depicted. In the above example, the second determiner includes the determiner 2322.

The region positional difference calculator may be configured to calculate the positional difference between the first region and the second region based on regions corresponding to the center of the iris or the center of gravity of the iris when the second determiner determines that the predetermined condition is satisfied. Furthermore, registration processor can be applied to the first distribution information and the second distribution information according to the positional difference calculated here. With such a configuration, the ophthalmologic apparatus can carry out registration of distribution information with reference to the center of the iris or the center of gravity of the iris, in the case where a good pupil image has not been acquired and a good iris image has been acquired.

On the other hand, when the second determiner determines that the predetermined condition is not satisfied, the region specifier may specify a region representing the iris pattern as each of the first partial image and the second partial image. Further, the region positional difference calculator may calculate the positional difference between the first region and the second region based on specified regions representing the iris pattern. Then, registration of distribution information can be carried out according to the positional difference calculated here. With such a configuration, the ophthalmologic apparatus can automatically proceed to a process using the iris pattern, in the case where both a good pupil image and a good iris image have not been acquired.

In the above example, the ophthalmologic apparatus first refers to the pupil images, then refers to the iris images when the pupil images are inappropriate. When the iris images are also inappropriate, the ophthalmologic apparatus refers to the iris pattern. However, the transition order of the referenced images is not limited to this example. For instance, the ophthalmologic apparatus of some embodiments may be configured to refer to pupil images or iris images at first, and then refer to the iris pattern when the pupil images or the iris images are inappropriate. A specific example thereof will be described below.

The region specifier of some embodiments may be configured to specify a combination of the first pupil image and the second pupil image each corresponding to the pupil or a combination of the first iris image and the second iris image each corresponding to the iris, as a combination of the first partial image and the second partial image. The ophthalmologic apparatus of some embodiments may further include the third determiner configured to determine whether a combination of the first pupil image and the second pupil image or a combination of the first iris image and the second iris image satisfies a predetermined condition. In the case of processing pupil images, the condition here may be, for example, any one of the followings: a condition that the difference between the size of the first pupil image and the size of the second pupil image is within a predetermined allowable range; and a condition that the size of the first pupil image and the size of the second pupil image both are within a predetermined allowable range. Further, in the case of processing iris images, the predetermined condition is, for example, that the entire circumference of the iris is depicted. In the above example, the third determiner includes the determiner 2322.

The region positional difference calculator may be configured to calculate the positional difference between the first region and the second region, based on regions corresponding to the center of the pupil or the center of gravity of the pupil, or based on regions corresponding to the center of the iris or the center of gravity of the iris, in the event that the third determiner determines that the predetermined condition is satisfied. Furthermore, registration can be applied to the first distribution information and the second distribution information according to the positional difference calculated here. With such a configuration, the ophthalmologic apparatus can carry out registration of distribution information with reference to the center of the pupil etc. in the case where good pupil images have been acquired, or with reference to the center of the iris etc. in the case where good iris images have been acquired.

On the other hand, when the third determiner determine that the predetermined condition is not satisfied, the region specifier may specify a region representing the iris pattern as each of the first partial image and the second partial image, and the region positional difference calculator may calculate the positional difference between the first region and the second region based on specified regions representing the iris pattern. Furthermore, registration of distribution information may be carried out according to the positional difference calculated here. With such a configuration, the ophthalmologic apparatus can automatically proceed to a process using the iris pattern in the case where the pupil images or the iris images acquired are inappropriate.

In some embodiments, the pupil size at the time of past examination can be reproduced. For example, in the case where the first front image has already been acquired and the second front image has not yet been acquired, the region specifier may specify a pupil image in the first front image corresponding to the pupil. The ophthalmologic apparatus of the present example includes a size calculator, an irradiation device, and an irradiation controller. The size calculator is configured to calculate a value representing the size of the pupil image specified by the region specifier. The value is, for example, a pupil diameter. In the above example, the size calculator includes the pupil size calculator 236. The irradiation device is configured for irradiating the subject's eye with visible light. In the above example, the irradiation device may include the illumination optical system 10, for example. The irradiation controller is configured to control the irradiation device to output the visible light having an intensity corresponding to the value calculated by the size calculator. In the above example, the irradiation controller includes the irradiation controller 213. According to the configuration of the present example, the ophthalmologic apparatus can irradiate the subject's eye with visible light and make the pupil smaller (i.e., cause miosis) so that the current pupil size of the subject's eye matches the pupil size when the first front image is obtained, that is, when the OCT scan for generating the first distribution information is performed.

In some embodiments, the registration of distribution information using the iris pattern can be optimized by performing OCT scanning and front image acquisition after having made the pupil of the subject's eye smaller (i.e., after having caused miosis). For example, the front image acquisition device acquires a front image of the anterior eye segment before the data acquisition device carries out data acquisition. The region specifier is configured to specify a pupil image corresponding to the pupil from the front image acquired. The ophthalmologic apparatus of the present example includes a size calculator, an irradiation device, and an irradiation controller. The size calculator is configured to calculate a value representing the size of the pupil image. The irradiation device is configured for irradiating the subject's eye with visible light. The irradiation controller is configured to control the irradiation device to output the visible light when the value calculated by the size calculator is equal to or less than a predetermined threshold value. The region specifier is configured to specify a region representing the iris pattern as each of the first region and the second region. Then, the ophthalmologic apparatus can perform registration of distribution information with reference to the iris pattern. According to such a configuration, the ophthalmologic apparatus can acquire a front image in a miotic state, that is, a front image with a large iris image. Therefore, the ophthalmologic apparatus becomes capable of appropriately carrying out the registration of distribution information based on the iris pattern.

The ophthalmologic apparatus of some embodiments may further include a difference processor configured to obtain difference information representing difference between the first distribution information and the second distribution information to which the registration has been applied by the registration processor. In the above example, the difference processor includes the difference processor 234. According to such a configuration, the ophthalmologic apparatus can obtain a difference between pieces of distribution information acquired at different times. The ophthalmologic apparatus may visualize and display the difference.

The embodiments described above are only examples of the present invention. Those who intend to implement the present invention may apply any modifications (e.g., omission, substitution, replacement, addition) within the scope of the gist of the present invention.

The invention claimed is:

1. An ophthalmologic apparatus comprising:
a data acquisition device that acquires data by scanning an anterior eye segment of a subject's eye using optical coherence tomography;
a distribution information generator that generates distribution information representing a distribution of a predetermined parameter in the anterior eye segment by analyzing the data;
a front image acquisition device that acquires a front image of the anterior eye segment at a time of the data being acquired;
a storage that stores first distribution information generated from first data acquired at a first time, a first front image at a time of the first data is being acquired, second distribution information generated from second data acquired at a second time, and a second front image at a time of the second data is being acquired;
a positional difference calculator that calculates a positional difference between the first front image and the second front image; and
a registration processor that applies registration to the first distribution information and the second distribution information based on the positional difference.

2. The ophthalmologic apparatus of claim 1, wherein the positional difference calculator comprises:
a region specifier that specifies a first region by analyzing the first front image, and specifies a second region corresponding to the first region by analyzing the second front image; and
a region positional difference calculator that calculates a positional difference between the first region and the second region as the positional difference between the first front image and the second front image.

3. The ophthalmologic apparatus of claim 2, wherein
the region specifier specifies a first partial image in the first front image corresponding to at least one site of a pupil and an iris, and specifies the first region based on the first partial image, and further
the region specifier specifies a second partial image in the second front image corresponding to the at least one site, and specifies the second region based on the second partial image.

4. The ophthalmologic apparatus of claim 3, wherein the region specifier specifies, for each of the first region and the second region, a region corresponding to at least one of a center of the pupil, a center of gravity of the pupil, a center of the iris, and a center of gravity of the iris, and/or, a region representing an iris pattern.

5. The ophthalmologic apparatus of claim 4, wherein
the region specifier specifies a first pupil image and a second pupil image each corresponding to a pupil, as the first partial image and the second partial image, and the ophthalmologic apparatus further comprises a first determiner that determines whether the first pupil image and the second pupil image satisfy a predetermined condition, wherein when the first determiner determines that the predetermined condition is satisfied, the region positional difference calculator calculates the positional difference between the first region and the second region based on regions each corresponding to the center of the pupil or the center of gravity of the pupil, and when the first determiner determines that the predetermined condition is not satisfied, the region specifier specifies a first iris image and a second iris image each corresponding to the iris, as the first partial image and the second partial image.

6. The ophthalmologic apparatus of claim 5, further comprising a second determiner that determines whether the first iris image and the second iris image satisfy a predetermined condition, wherein when the second determiner determines that the predetermined condition is satisfied, the region positional difference calculator calculates the positional difference between the first region and the second region based on regions each corresponding to the center of the iris or the center of gravity of the iris, and when the second determiner determines that the predetermined condition is not satisfied, the region specifier specifies regions each representing the iris pattern as the first partial image and the second partial image, and the region positional difference calculator calculates the positional difference between the first region and the second region based on the regions each representing the iris pattern.

7. The ophthalmologic apparatus of claim 4, wherein the region specifier specifies a first pupil image and a second pupil image each corresponding to the pupil, or a first iris image and a second iris image each corresponding to the iris, as the first partial image and the second partial image, and the ophthalmologic apparatus further comprises a third determiner that determines whether a combination of the first pupil image and the second pupil image or a combination of the first iris image and the second iris image satisfies a predetermined condition, wherein when the third determiner determines that the predetermined condition is satisfied, the region positional difference calculator calculates the positional difference between the first region and the second region, based on regions each corresponding to the center of the pupil or the center of gravity of the pupil, or based on regions each corresponding to the center of the iris or the center of gravity of the iris, and when the third determiner determines that the predetermined condition is not satisfied, the region specifier specifies regions each representing the iris pattern as the first partial image and the second partial image, and the region positional difference calculator calculates the positional difference between the first region and the second region based on the regions each representing the iris pattern.

8. The ophthalmologic apparatus of claim 2, wherein when the first front image has already been acquired and the second front image has not yet been acquired, the region specifier specifies a pupil image in the first front image corresponding to the pupil, and the ophthalmologic apparatus further comprises:

a size calculator that calculates a value representing a size of the pupil image;

an irradiation device for irradiating the subject's eye with visible light; and an irradiation controller that controls the irradiation device to output the visible light having an intensity corresponding to the value calculated by the size calculator.

9. The ophthalmologic apparatus of claim 4, wherein the front image acquisition device acquires the front image of the anterior eye segment before the data acquisition device acquires the data, the region specifier specifies a pupil image in the front image corresponding to the pupil, and the ophthalmologic apparatus further comprises:

a size calculator that calculates a value representing a size of the pupil image;

an irradiation device for irradiating the subject's eye with visible light; and an irradiation controller that controls the irradiation device to output the visible light when the value calculated by the size calculator is equal to or less than a predetermined threshold value, wherein the region specifier specifies regions each representing the iris pattern as the first region and the second region.

10. The ophthalmologic apparatus of claim 1, wherein the front image acquisition device comprises an image sensor for photographing the anterior eye segment from a front direction or an oblique direction.

11. The ophthalmologic apparatus of claim 1, wherein the data acquisition device scans a three dimensional region of the anterior eye segment, and the front image acquisition device comprises a processor that generates the front image from three dimensional data acquired by a scan of the three dimensional region.

12. The ophthalmologic apparatus of claim 1, wherein the predetermined parameter comprises at least one of a parameter representing a corneal thickness and a parameter representing a corneal shape.

13. The ophthalmologic apparatus of claim 1, further comprising a difference processor that obtains difference information between the first distribution information and the second distribution information to which the registration has been applied by the registration processor.

* * * * *